United States Patent [19]
Johnson

[11] Patent Number: 5,842,968
[45] Date of Patent: Dec. 1, 1998

[54] SOFT PENILE CLAMP DEVICE

[76] Inventor: Robert E. Johnson, 35 Elmcrest Ave., Providence, R.I. 02908

[21] Appl. No.: 696,394

[22] Filed: Aug. 14, 1996

Related U.S. Application Data

[60] Provisional application No. 60/002,465 Aug. 16, 1995.
[51] Int. Cl.⁶ .................................................. A61F 5/00
[52] U.S. Cl. ........................... 600/38; 128/842; 128/885; 128/DIG. 25
[58] Field of Search ................................... 128/842, 844, 128/918, 885, DIG. 25; 600/38–41

[56] References Cited

U.S. PATENT DOCUMENTS

| 678,943 | 7/1901 | Davis | 128/885 |
|---|---|---|---|
| 3,636,948 | 1/1972 | Atchley | 600/41 |
| 3,866,611 | 2/1975 | Baumrucker | 128/885 |
| 5,327,910 | 7/1994 | Flynn | 128/842 |

*Primary Examiner*—Michael A. Brown
*Attorney, Agent, or Firm*—Robert J Doherty

[57] ABSTRACT

The invention is an improved clamp device to be used by males having little or no control over the leakage of urine. The device can be easily applied and adjusted to the most comfortable fit while achieving its purpose with less discomfort and bulk of present devices.

13 Claims, 5 Drawing Sheets

SOFT PENILE CLAMP DEVICE

This application claims the benefit of U.S. Provisional Application Ser. No. 60/002,465 filed Aug. 16. 1995.

BACKGROUND OF THE INVENTION

The incident of incontinence in men has sharply increased as the result of the increase in prostate cancer and the treatment by surgery and radiation that results in damage to the nerves that control the function of the sphincter muscle which controls the flow of urine from the bladder through the urethra. Additionally, nerve endings that control the supply of blood to the penis are also damaged causing a sharp reduction in the amount of blood being retained in the penis causing the penis to be reduced both in length and firmness.

Existing devices have the tendency to slip off or need to be compressed so tightly as to further reduce the supply of blood to the penis which in time could cause irreversible damage to that organ.

My invention, an improvement over prior art, addresses both the problem of slippage and the ability to shut off the flow of urine through the urethra by a more gentle and comfortable means allowing for a longer period of use without restricting the flow of blood through the central arteries of the penis. A measure of control of urine flow can be obtained with the device properly fitted in place by squeezing the sides of the device together thus transferring the pressure from the lumen area to the sides and allowing for the flow of urine as well as being able to utilize the stop-start function of the exercises necessary to strengthen the sphincter muscle in the development of a more normal control of bladder function.

DESCRIPTION OF PRIOR ART

A clamp that is presently used includes a device that is surgically implanted which has as its closer an inflatable cuff placed around the penis inside the body and connected by tubing to a reservoir of fluid also within the body cavity, and said reservoir connected to a pump/switch device inserted within the scrotum. To activate, the user presses the pump forcing the fluid to move from the reservoir to the cuff, building up pressure in the cuff around the penis, blocking the flow of urine, pressing again allows the fluid to return to the reservoir releasing the pressure in the cuff, allowing the urine to be expelled. Any malfunction of this device would require invasive surgery to correct.

Also, presently in common use is a non-invasive clamp including a device having two parallel cushions attached to ridged strips that are hinged at one end. To use, the individual opens the device and places it over the penis, bringing together the open ends of the device and securing said ends together. The clamp is bulky, slips off the penis and requires excessive pressure to achieve its goal of stopping the flow of urine. This device when used in that manner also restricts the flow of blood into the organ resulting in very limited use of the device. A device similar to the above is also illustrated in U.S. Pat. No. 3,203,421 to Bialick issued Aug. 31, 1965. Other clamp-type and other related male incontinence devices are shown and illustrated by the following U.S. patents: U.S. Pat. No. 678,943 to Davis dated Jul. 23, 1901; U.S. Pat. No. 2,533,924 to Foley dated Dec. 12, 1950; U.S. Pat. No. 2,756,753 to Means dated Jul. 31, 1956; U.S. Pat. No. 3,147,754 to Koessler dated Sept. 8, 1964; and U.S. Pat. No. 4,880,016 to Worthetal dated Nov. 13, 1989. Generally, these above indicated external clamp-type devices act in a transversal direction upon the penis in an attempt to concentrate the closure force to thus effect collapse of the urethra.

Despite the existence of both the implant and external clamp-type devices as above indicated, there is a continuing need for an effective, inexpensive and more comfortable device of this nature and providing such is a primary object of the present invention.

SUMMARY OF THE INVENTION

In summary, this device when used will bring relief to the incontinent male of embarrassing urine leakage and the expense and discomfort of having to replace bulky wet pads.

The advantage of this device over present clamps is that its use does not require surgery to insert or repair, it is not bulky and can be used over long periods without discomfort.

In accordance with the above shortcomings and disadvantages of the prior art, the object of the present invention is the provision of a more genital considerate and more effectively functional device comprising a length of cushion material forming a member having means to connect the ends thereof releasably to form a ring around the penis in a constricting relation with a key ridge in place longitudinally along a length of the urethra and directly under the lumen. The remaining cushion material applies a counter pressure sufficient to cause the key ridge to press in on the lumen thereby collapsing it upon itself a longitudinally sufficient distance to effectively contain the flow of urine therein.

Other objects, features and advantages of the invention shall become apparent as the description thereof proceeds when considered in connection with the accompanying illustrative drawings.

BRIEF DESCRIPTION OF THE DRAWINGS

In the drawings which illustrate the best mode presently contemplated for carrying out the present invention.

DESCRIPTION OF THE PREFERRED EMBODIMENTS

Figure 1:
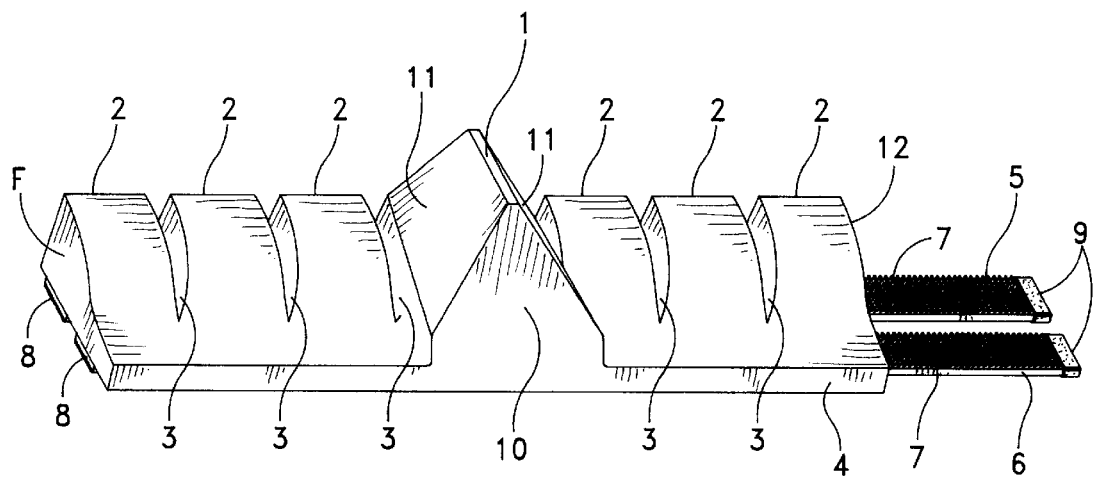
FIG. 1 shows a front view of the device in an opened laid-out position for illustration.

FIG. 1 shows a preferred form of the device of the present invention in an opened laid-out front perspective view position. Therein a cushion 12 is depicted as having a ridge key portion 1. The cushion further includes lateral sides F and a bottom wall 12. The cushion laterally terminates at such opposed faces F and includes high portions 2 through which "V" notches 3 are formed which notches close up when the device is wrapped around the penis P. The lower edge 4 of the cushion 12 faces towards the body AB in use. A first strap 5 is attached to the back side of the cushion. In addition, a second strap 6 is also attached to the back side of the cushion and centered between the widest part of the cushion and the inner edge thereof. A Velcro® hook strip 7 is attached to the inner face of straps 5 and 6. A rubber lift tab 9 is attached at the end of each of the hook strips.

Figure 5:
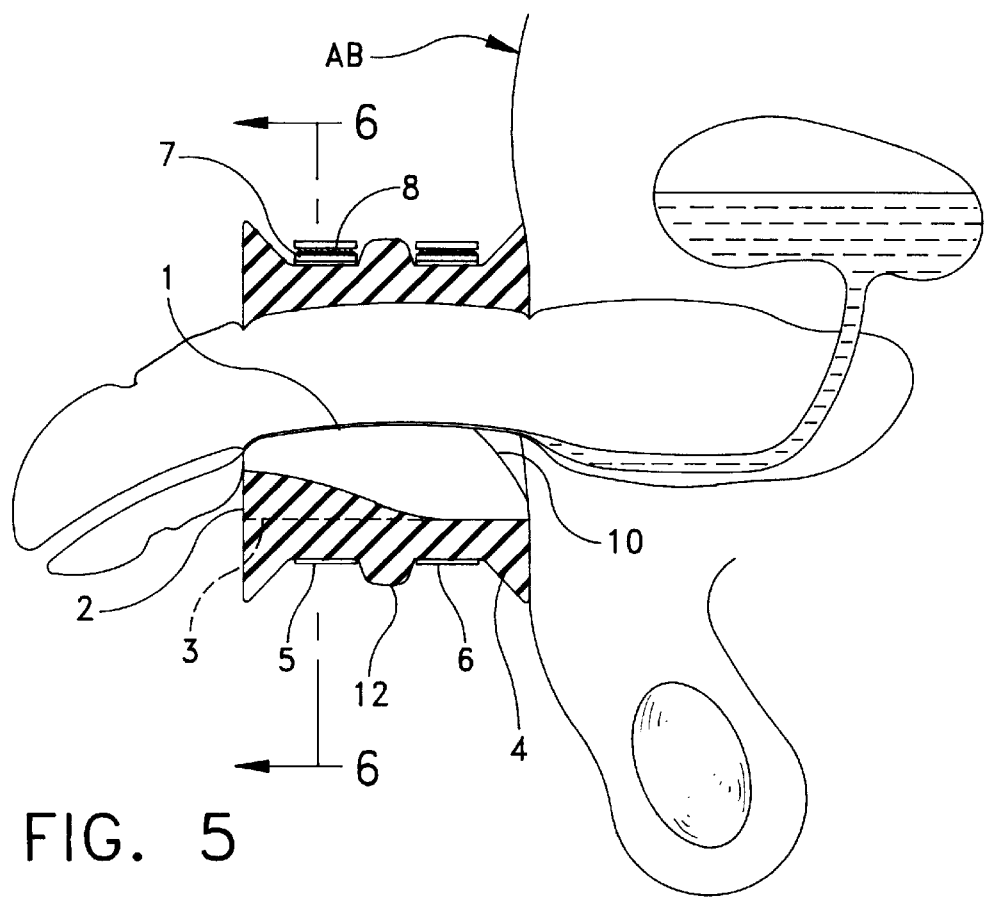
FIG. 5 is a cross-sectional view of FIG. 4 showing the position of the key ridge as it is compressed.

The inner face 10 of the key ridge 1 is adapted to be positioned adjacent the wearer's body AB when the device is worn on the penis P as best shown in FIG. 5. The key ridge includes sides 11 descending from the top down on each side of the key ridge to the upper portion of the base of the cushion 12.

Figure 2:
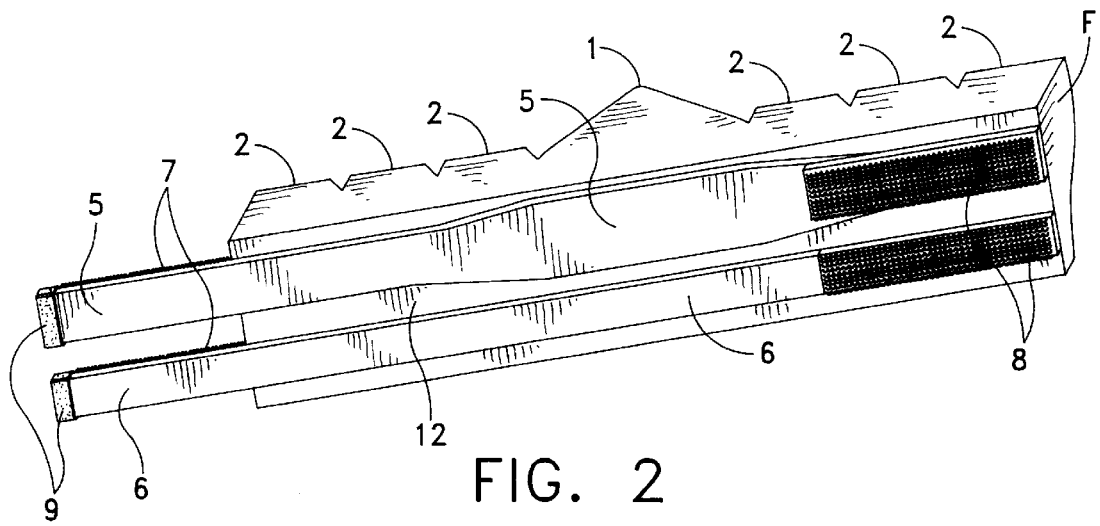
FIG. 2 shows a bottom view of the device with two straps of dissimilar width and the wider of the two positioned under the key ridge.
Figure 3:
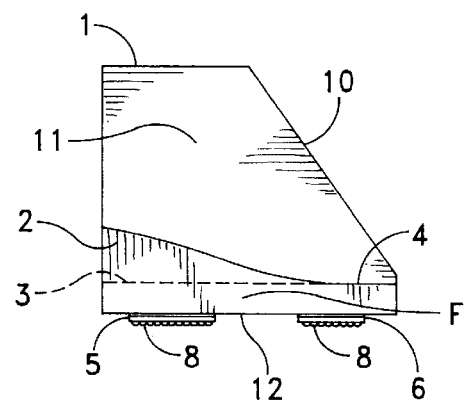
FIG. 3 is an end view taken from the left side of FIG. 1 showing the key ridge, the depth of the "V" cuts, the angle and thickness of the cushion material back to front and the position of the straps.

Referring now to FIG. 2 which it should be noted is a bottom perspective view of the device rotated 180° from FIG. 1, Velcro® loop strips 8 are attached to strap 5 and positioned centrally under the key ridge 1 and strap 6 secured in a parallel manner to the outer face of the cushion 12. It should be also noted that in the end view of the device as shown in FIG. 3 that the position of the key ridge 1 over strap 5 is best shown. Also, the high portions 2 of the cushion 12 on the left side of the device angle downwardly and towards the right and terminate in the lower face portion 4 of the cushion.

Figure 4:
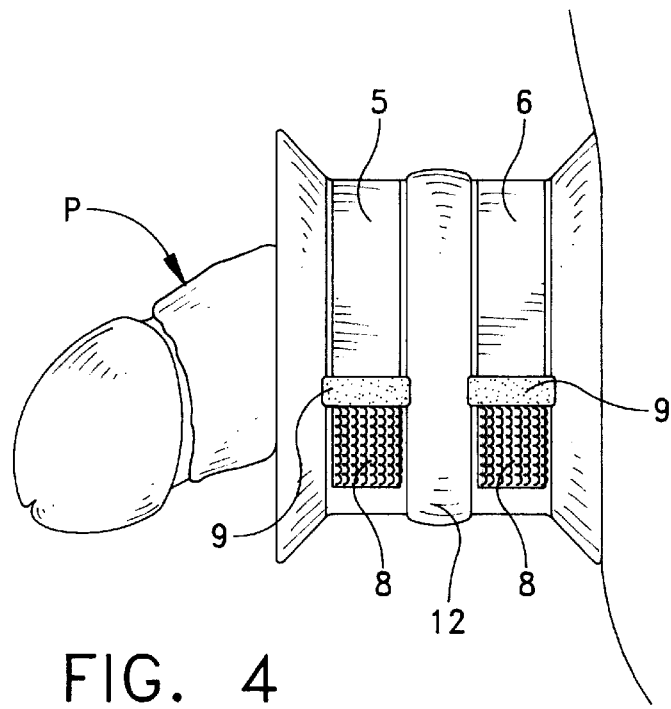
FIG. 4 shows the device as it would be attached to the penis when in use.
Figure 6:
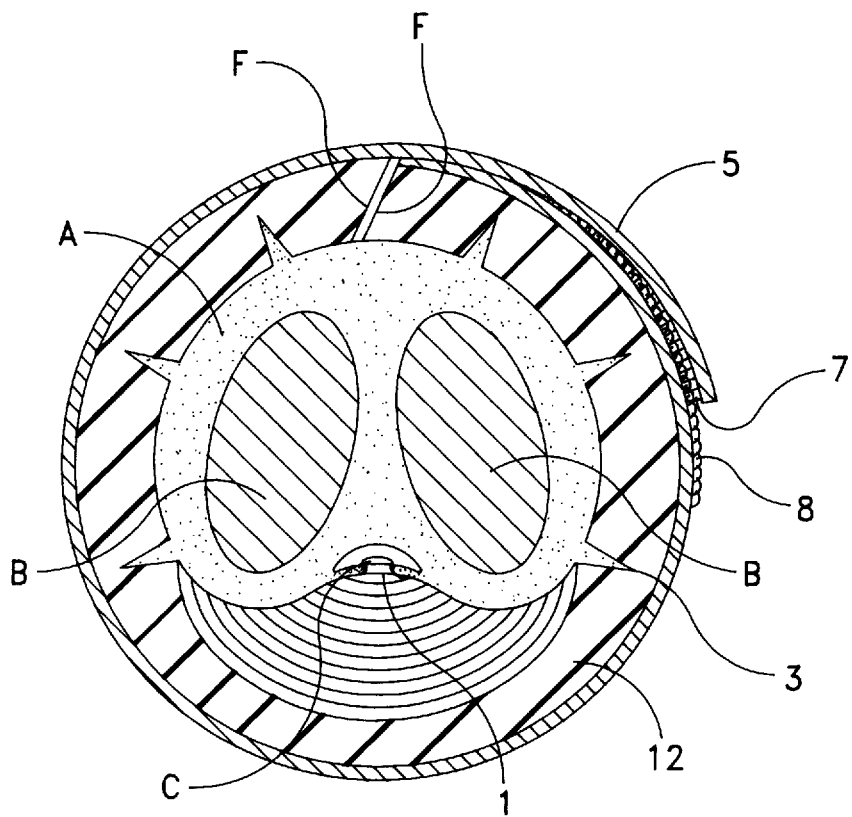
FIG. 6 is a cut-a-way view of the device in place taken along the line of 6—6 in FIG. 5.

When the device is fitted around the penis as shown in FIGS. 4 through 6, the wide strap 5 encircles the cushion 12 and is also secured to the Velcro® loop strip 8. The second strap 6 also encircles the cushion and likewise is secured to the Velcro® loop strap 8 associated with such strap 6. When properly positioned, the key ridge 1 is compressed as it closes off the flow of urine from the bladder through the urethra, that is, the key ridge 1 is compressed underneath the penis in position to be compressed against the urethra. In such position, the low face portion 4 of the cushion is placed against the body, and the wide portion of strap 5 positioned opposite the key ridge 1 whereas the position of the second supporting strap 6 is closer to the body AB. When the hook 7 and the loops 8 are engaged in the penis wrapped position shown in FIG. 5, the cushion is compressed and such compression affords the desired collapsing of the urethra along a significant length thereof defined by at least the length of the key ridge 1 as shown. The bottom of the cushion 12 may also be placed in a compressed state as shown by its enlargement between the straps 5 and 6 in FIGS. 4 and 5.

Referring now to FIG. 6, a cut-a-way view of the device in place taken along line 6—6 of FIG. 5 is shown and depicts the outer section of the penile organ A, the corpora cavernosa B in a relaxed position and the urethra C shown in a closed position being held in that state by compression via the key ridge 1. Such state is further supported all around by cushion 12 secured in place by Velcro® hook 7 and loop 8 device attached to strap 5. It should also be pointed out that while the cushion and faces F are shown abutting each other, they could overlap or be spaced from each other to accommodate varying penis circumferences.

Figure 7:
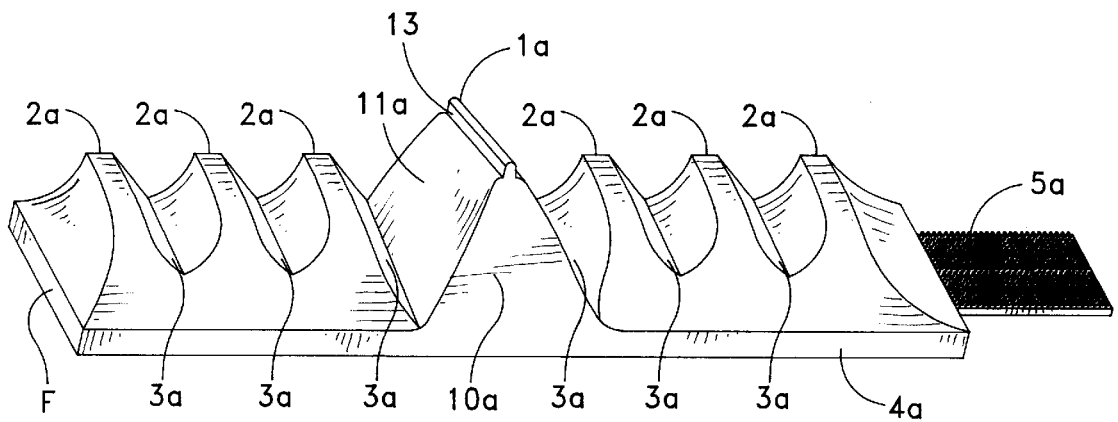
FIG. 7 shows an alternate form of the invention in which more pronounced "V" cuts are utilized and in which one rather than two straps may be utilized in an opened laid-out position similar to the illustrative form shown in FIG. 1.

A modified form of the device is shown in FIG. 7 in an opened laid-out front position in which the key ridge 1a of the cushion 12a is of a modified form. In addition, the ridge portions 2a are of modified form including notched portions or "V" cuts 3a. The lower edge or face 4a of the cushion which edge faces towards the body AB is also depicted. The Velcro® hook strap 5a is attached to the back of the cushion. The inner face 10a of the key ridge is also positioned so as to be adjacent the body as best shown in FIG. 5 with the preferred embodiment. The sides 11a of the key ridge 1a descend from the top down on each side of the ridge below a vertical step 13 of the ridge. Such vertical step 13 of the key ridge engages the urethra along the length of the key ridge 1a when the modified form of the device is wrapped around the penis in the same fashion as explained with regards to FIGS. 1 through 6 of the drawings.

Figure 9:
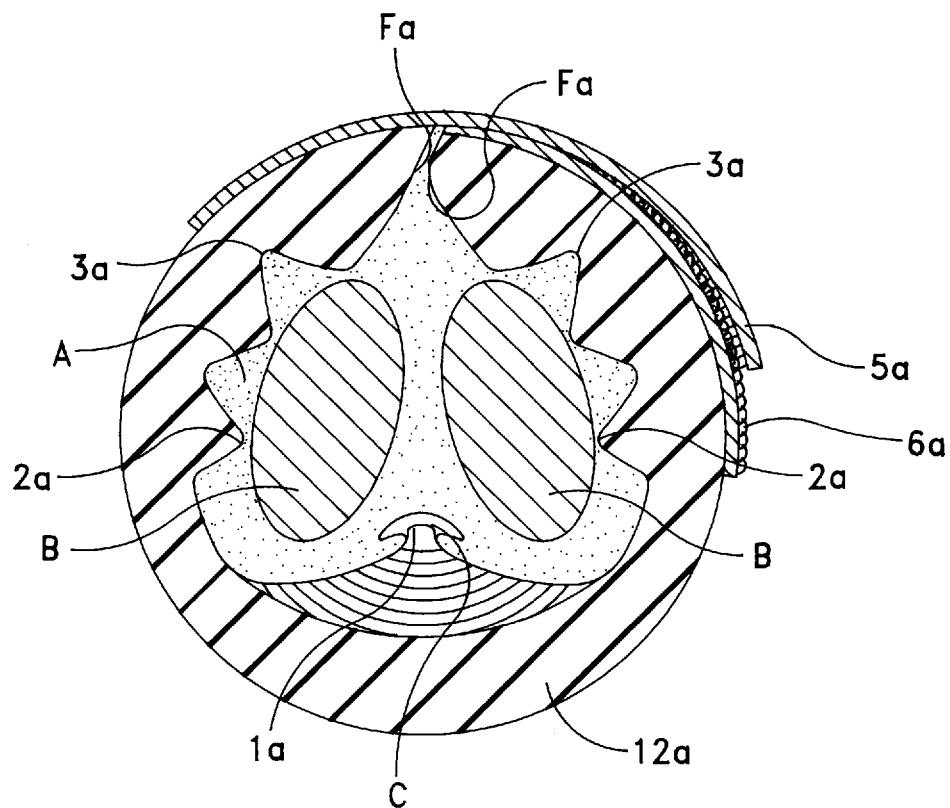
FIG. 9 is a cross-sectional view of a penis with the device of FIG. 7 in functional place similar to the view shown by FIG. 6 in the FIGS. 1–6 embodiment and in which the compression of the key ridge and the position of the "V" cuts are illustrated.

A further modification of the device shown in FIG. 7 includes a Velcro® loop strip attached to the outer face of the cushion as viewed from the as applied position in FIG. 9 and a single wider Velcro® hook strip 5a attached to and extending beyond the cushion with the hook portion of the strip facing the inner portion of the cushion.

The FIG. 9 cut-a-way view of the device shown in FIG. 7 shows the outer section of the penile organ A, the position of the corpora cavernosa B in a relaxed state and the urethra C shown in a closed position. Such urethra closed position being held in that state by key ridge 1a supported around the underside by cushion 12a and around the sides and top by the ridges of the "V" cuts 2a with the notched portions of such "V" cuts allowing for blood flow through the member while the device is in place on the penis. It should also be pointed out that while the cushion and faces of Fa are shown abutting each other, they could overlap or be spaced apart from each other to accommodate varying penis circumferences.

Continuing with the description of the invention, the device comprises a waterproof non-allergenic preferably latex foam material shaped with a high pointed ridge generally disposed at equal distances from both ends and slanting out and down transversely towards said ends with the ridge extending half the longitudinal distance from the outer edge then downwardly and outwardly with the base of said material extending from the outer edge to the base of said material extending from the outer edge to the inner edge coming to two points at said base. The density of the foam material is preferably greater at the ridge position and lesser on either side of said ridge. The cushion material may be any suitable latex or plastic foam material or other suitably soft and compressive material and may be cut or otherwise formed including direct molding into the desired shape or include a backing of tape-like material such as fabric onto which the cushion material is attached either by adhesive or other known means.

The mass, that is, the amount or volume, of the cushion material is also preferably greater along the outer edge of the device descending in mass from the base of the high, that is, the key, ridge outwardly towards both ends equally as well as inwardly to the inner edge of said cushion, said cushion is formed with "V" notches extending inwardly from the outer edge on the face side of the cushion in sufficient numbers on either side equally to allow said cushion to encircle the penis without bunching up. The device having sufficient overlap of material can be adjusted to accommodate the organ of the male with a degree of constriction necessary to achieve the desired results.

Figure 8:
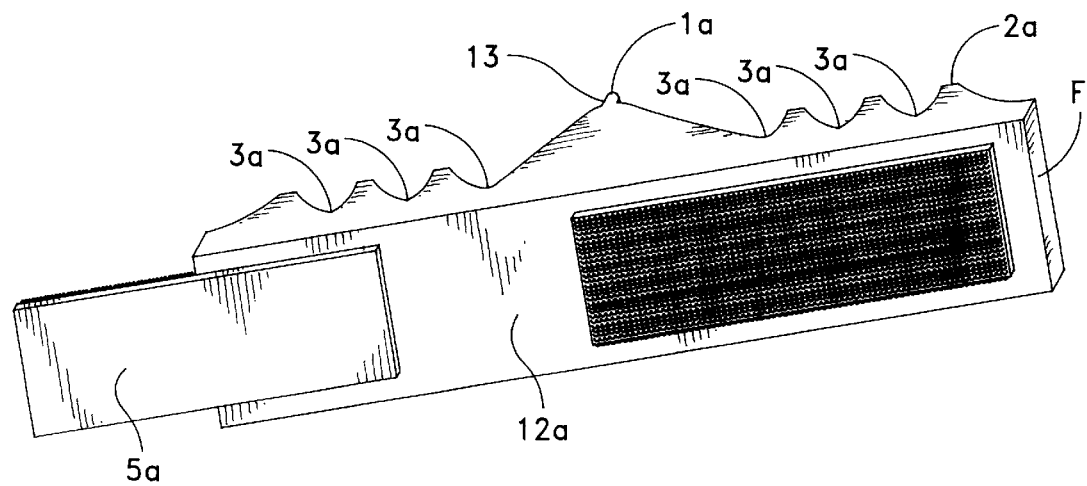
FIG. 8 is a bottom view of the FIG. 7 embodiment.

Said cushion is preferably backed with a first strap 5 of not less than one quarter the width of the cushion and widening to a width of not less than one half the width of the cushion at a point directly beneath the highest point of the key ridge thence decreasing again to a width of one quarter the width of the cushion and extending beyond said cushion a distance of not less than one quarter the length of said cushion. This extension having secured to it on the inner face a Velcro® hook strip of the same length of the extended strap. A second strap of not less than one quarter the width of the cushion is secured to the back of the cushion along but not butting up to the inner edge of the cushion. This strap also extends beyond the cushion a length equal to that of the first strap also having secured to its inner face a Velcro® hook strip of the same length as the extended strap. Both straps having on their opposite ends a Velcro® loop strip secured to the outer face of each strap of such a length to accommodate the opposing hook strips attached to the opposite end of said strap. When the clamp is placed in position with the key ridge directly beneath and along the area of the urethra, the hook end of the straps are folded over and attached to the corresponding Velcro® loop strips holding the device securely in place. The significance of utilizing two separate straps with the first one thereof having a greater bearing width beneath the key ridge portion of the cushion 12 is that such is believed to impart a more clamping force to the key ridge and thus the urethra but other strap configurations including the use of a single strap is possible as shown in FIGS. 7–9.

The length and position of the key ridge is significant in that it allows a more gentle closure pressure to be applied to the lumen and to be dispersed along the length of the lumen rather than transversely across its width as with all prior methods and as illustrated in prior U.S. Pat. Nos. 2,756,753; 3,147,754; 3,203,421; and 4,880,016. The advantage over prior art is the ability of the compressed sponge action of the key ridge to adjust to the changes of the body member in keeping a gentle pressure along the corpus spongiosum channel allowing for extended use. This longitudinal application of the force along with the shape of the key ridge in direct longitudinal contact with the penis are believed to contribute to the improved operation of the subject device.

There are also effective differential pressures albeit gentle when compared to prior art devices applied to different portions of the penis. Since the key ridge 1 or 1a is substantially higher than the ridges 2 or 2a, the circumferential closure of the device in use enables the key ridge to differentially apply greater pressure to the penis than the other ridges so as to effectively block off the urethra yet enable the blood carrying vessels to remain open. Adjustment of the key ridge shape also contributes to such with the smaller cross-sectional extent of the key ridge 1a able to apply a more concentrated force to the urethra while the extent of the "V" cuts 3 and 3a permit a complete closure of the device and effective urethra shut off enabling selective distortion of penis outer portions into the cuts especially in the case of the wider cuts 3a so that the corpora cavernosa remain open. In addition, the foam material forming the key ridge may be denser than the material forming the other ridges.

Similarly, the longitudinal orientation of the key ridge and its longitudinal application of force to the urethra enables a lesser force which when applied over a greater distance to achieve effective flattening of the urethra. The inward outward slant of the ridges especially the key ridge enables a closer body positioning of the device for both comfort, reduced bulk appearance and maximizing effective penis length for mounting the device.

Also while it has been described that the key ridge is generally centrally longitudinally positioned in the cushioning material or member and while that is obviously the preferred position, it could be otherwise located, i.e., offset or at one of the ends of the member, so long as the fitment of the device around the penis positioned the key ridge in its correct position under and proximal to the urethra.

While there is shown and described herein certain specific structure embodying this invention, it will be manifest to those skilled in the art that various modifications and rearrangements of the parts may be made without departing from the spirit and scope of the underlying inventive concept and that the same is not limited to the particular forms herein shown and described except insofar as indicated by the scope of the appended claims.

What is claimed is:

1. An external clamping device adapted for pressure applying circumferential fitment to its active position around a human penis proximal to that portion of the human body from which the penis extends, comprising a flexible elongated member having opposed inner and outer sides and of a length sufficient to at least circumferentially extend about said penis and of a width less than the length of said penis, said member inner surface including cushioning material of a thickness sufficient to cushion yet circumferentially squeeze said penis and wherein said cushioning material further including a plurality of serially extending longitudinally spaced upwardly laterally extending ridges and downwardly laterally extending notches therebetween, one of said ridges being a key ridge extending upwardly substantially higher than the other ridges and upwardly terminating in a narrow laterally extending ridge peak, said ridge peak adapted for positioning proximal to, directly beneath and longitudinally aligned with the penile urethra when the device is circumferentially wrapped under pressure around the penis to an active position such that the ridge peak differentially applies pressure to the urethra to collapse such while the remaining ridges apply lesser pressure to the penis portions other than that proximal to the urethra so as to enable the corpora cavernosa to remain open for the flow of blood therethrough and means for securing said member in its active pressure applying position.

2. The device of claim 1 wherein said key ridge is centrally longitudinally positioned on said member.

3. The device of claim 2, said means for securing said member to its active position being a pair of straps positioned on the outer side of said member, one of said straps of a width at least equal to that of the lateral extent of said key ridge peak and positioned in superposed relation to the center of the ridge peak and extending beyond the longitudinal extent of said member to define a connecting strap end, such connecting strap end adapted for detachable connection to a receiving connection pad attached to the member outer side.

4. The device of claim 3, said cushion on either side of the key ridge having several notches that when applied to the penis would close applying a firm even pressure opposing the pressure applied at the point of the key ridge effectively closing off the opening of the lumen stopping the flow of urine.

5. The device of claim 3, said strap for securing said cushion to said penis being wider in its center and of lesser width towards each end and attached to said member directly opposite the key ridge and having secured to said strap two strips of interlocking hook and loop material to temporarily secure said device to said penis.

6. The device of claim 2, said cushioning material on either side of the key ridge having a greater mass away from the human body and a lesser mass towards the body adding to and being a part of the holding property of said device on the penis.

7. The device of claim 1, said key ridge of the cushion material having defining sides which meet at said peak in a sharp angular relation.

8. The device of claim 1, said key ridge of the cushion material having a greater mass away from the human body and a lesser mass adjacent to the body to increase the holding property of said device to the penis.

9. The device of claim 1, said ridges being formed of a foam material, and wherein the foam material forming the key ridge is denser than the material forming the other ridges.

10. The device of claim 1 wherein said notches are of a longitudinal extent such that the intermediate ridges are circumferentially spaced from each other in the active pressure applied position of the device.

11. The device of claim 10 wherein said notches are generally "V" shaped.

12. The device of claim 1, said key ridge peak being a flat narrow surface in part defined by a pair of upwardly inwardly slanted surfaces.

13. The device of claim 12, said key ridge peak further defined by a pair of longitudinally separated laterally extending generally parallel walls.

* * * * *